(12) United States Patent
Gelbard et al.

US011661409B1

(10) Patent No.: US 11,661,409 B1
(45) Date of Patent: *May 30, 2023

(54) ACID ADDITION SALTS, COMPOSITIONS, AND METHODS OF TREATING

(71) Applicant: Pioneura Corporation, Fairport, NY (US)

(72) Inventors: Harris A. Gelbard, Pittsford, NY (US); John M. McCall, Boca Grande, FL (US); Jesse Damsker, Alexandria, VA (US); Arthur Romero, Chesterfield, MO (US)

(73) Assignee: Pioneura Corporation, Fairport, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/931,688

(22) Filed: Sep. 13, 2022

Related U.S. Application Data

(63) Continuation-in-part of application No. 17/588,847, filed on Jan. 31, 2022, now Pat. No. 11,479,541.

(51) Int. Cl.
*C07D 401/04* (2006.01)
*C07D 471/04* (2006.01)

(52) U.S. Cl.
CPC ......... *C07D 401/04* (2013.01); *C07D 471/04* (2013.01)

(58) Field of Classification Search
CPC .................................................. C07D 401/04
USPC .................................................. 514/255.05
See application file for complete search history.

(56) References Cited

U.S. PATENT DOCUMENTS

| | | | |
|---|---|---|---|
| 8,846,909 B2 | 9/2014 | Gelbard | |
| 8,877,772 B2 | 11/2014 | Gelbard | |
| 9,181,247 B2 | 11/2015 | Gelbard | |
| 9,814,704 B2 | 11/2017 | Gelbard | |
| 10,485,800 B2 | 11/2019 | Gelbard | |
| 11,479,541 B1 * | 10/2022 | Gelbard | C07D 401/04 |
| 2016/0024087 A1 | 1/2016 | Gelbard | |
| 2021/0040091 A1 | 2/2021 | Stockwell | |
| 2021/0100803 A1 | 4/2021 | Yesilkanal | |

FOREIGN PATENT DOCUMENTS

EP          2379561      10/2011

OTHER PUBLICATIONS

Bellizzi, M. et al., "The Mixed-Lineage Kinase Inhibitor URMC-099 Protects Hippocampal Synapses in Experimental Autoimmune Encephalomyelitis", 5(6):ENEURO.0245-18, (2018).
Dong, W. et al., "The mixed-lineage kinase 3 inhibitor URMC-099 facilitates microglial amyloid-β degradation", J Neuroinflammation. , 13(1):184, (2016).
Gnanadhas, D. et al., "Autophagy facilitates macrophage depots of sustained-release nanoformulated antiretroviral drugs", J Clin Invest., 127(3):857-73, (2017).
Goodfellow, V. et al., "Discovery, Synthesis and Characterization of an Orally Bioavailable, Brain Penetrant Inhibitor of Mixed Lineage Kinase 3", J Med Chem., [Epub ahead of print], (2013).
Kiyota, T. et al., "URMC-099 facilitates amyloid-β clearance in a murine model of Alzheimer's disease", J Neuroinflammation, 15(1):137, (2018).
Kyoko, T. et al., "Mixed-lineage kinase 3 pharmacological inhibition attenuates murine nonalcoholic steatohepatitis", JCI Insight., 2(15):e94488, (2017).
Marker, D. et al., "The new small-molecule mixed-lineage kinase 3 inhibitor URMC-099 is neuroprotective and anti-inflammatory in models of human immunodeficiency virus-associated neurocognitive disorders", J Neurosci., 33(24):9998-10010, (2013 ).
Miller-Rhodes, P. et al., "The broad spectrum mixed-lineage kinase 3 inhibitor URMC-099 prevents acute microgliosis and cognitive decline in a mouse model of perioperative neurocognitive disorders", J Neuroinflammation, 16(1):193, (2019).
Polesskaya, O. et al., "MLK3 regulates fMLP-stimulated neutrophil motility", Mol Immunol., 58(2):214-22, (2014).
Rhoo, K. et al., "Pharmacologic inhibition of MLK3 kinase activity blocks the in vitro migratory capacity of breast cancer cells but has no effect on breast cancer brain metastasis in a mouse xenograft model", PLoS One, 9(9):e108487, (2014).
Saminathan, P. et al., "Broad Spectrum Mixed Lineage Kinase Type 3 Inhibition and HIV-1 Persistence in Macrophages", J Neuroimmune Pharmacol., 14(1):44-51, (2019).
Stahl, P. et al., "Handbook of Pharmaceutical Salts. Properties, Selection and Use", (Wiley-VCH), pp. 265-327. (2008).
Thomas, M. et al., "Modulating cellular autophagy for controlled drug release", Nanomedicine, 13(17):2139-54, (2018).
U.S. Appl. No. 17/588,847; Applicant-Initiated Interview Summary, dated Jul. 18, 2022; 2 pages.
U.S. Appl. No. 17/588,847; Non-Final Office Action, dated May 11, 2022; 15 pages.
U.S. Appl. No. 17/588,847; Notice of Allowance, dated Aug. 8, 2022; 7 pages.
Zhang, G. et al., "The mixed lineage kinase-3 inhibitor URMC-099 improves therapeutic outcomes for long-acting antiretroviral therapy", Nanomedicine., 12(1):109-22, (2016).

(Continued)

*Primary Examiner* — Kahsay Habte
(74) *Attorney, Agent, or Firm* — Cynthia Hathaway; Lauren L. Stevens

(57) ABSTRACT

Provided is a tartrate salt of 3-(1H-indol-5-yl)-5-[4-[(4-methyl-1-piperazinyl)methyl]phenyl]-1H-pyrrolo[2,3-b]pyridine and crystalline forms thereof. Also provided are pharmaceutical compositions comprising a tartrate salt disclosed herein and crystalline forms thereof and a pharmaceutically acceptable excipient, and a method of treating a disease or disorder, such as disease or disorder associated with neuroinflammation, comprising administering to a subject in need thereof, a therapeutically effective amount of an acid addition salt disclosed herein or the pharmaceutical composition of the acid addition salt.

6 Claims, 2 Drawing Sheets

(56) References Cited

OTHER PUBLICATIONS

Zhao, H. et al., "Correction to: Synergism between the phosphatidylinositol 3-kinase p110β isoform inhibitor AZD6482 and the mixed lineage kinase 3 inhibitor URMC-099 on the blockade of glioblastoma cell motility and focal adhesion formation", Cancer Cell Int., 21(1):403, (2021).

Zhao, H. et al., "Synergism between the phosphatidylinositol 3-kinase p110β isoform inhibitor AZD6482 and the mixed lineage kinase 3 inhibitor URMC-099 on the blockade of glioblastoma cell motility and focal adhesion formation", Cancer Cell Int., 21(1):24, (2021).

* cited by examiner

ACID ADDITION SALTS, COMPOSITIONS, AND METHODS OF TREATING

This application is a Continuation-in-Part of U.S. Non-Provisional application Ser. No. 17/588,847, filed Jan. 31, 2022, the disclosure of which is hereby incorporated by reference as if written herein in its entirety.

Compound 1, (3-(1H-indol-5-yl)-5-[4-[(4-methyl-1-piperazinyl)methyl]phenyl]-1H-pyrrolo[2,3-b]pyridine), is an orally bioavailable, brain penetrant mixed lineage kinase (MLK) inhibitor with $IC_{50}$ of 19 nM, 42 nM, 14 nM, and 150 nM, for MLK1, MLK2, MLK3, and Mitogen-activated protein kinase 12 (DLK), respectively. Compound 1 also inhibits leucine-rich repeat kinase 2 (LRRK2) activity with $IC_{50}$ of 11 nM and tyrosine-protein kinase ABL1 with IC50 of 6.8 nM. Compound 1 induces autophagy in in vitro and in vivo models. Compound 1 inhibits lipopolysaccharide-induced tumor necrosis factor alpha (TNFα) release in microglial cells and 1HV-1 Tat-induced release of cytokines in human monocytes.

Compound 1

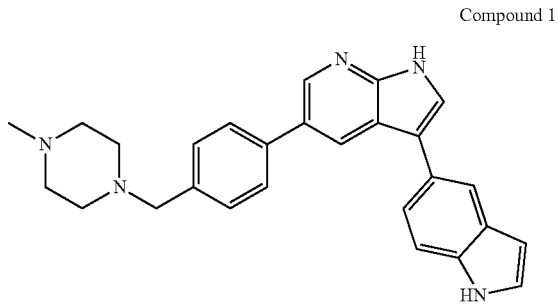 [SMILES: CN1CCN(Cc2ccc(-c3cnc4[nH]cc(-c5ccc6[nH]ccc6c5)c4c3)cc2)CC1]

In vitro, Compound 1 additionally prevents destruction and phagocytosis of cultured neuronal axons by microglial cells. Compound 1 reduces N-formylmethionyl-leucyl-phenylalanine (fMLP)-induced chemotaxis of wild-type neutrophils in vitro. In mice, Compound 1 shows excellent pharmacokinetic properties and central nervous system (CNS) penetration compatible with BID or qD dosing. Compound 1 (10 mg/kg i.p.) reduced inflammatory cytokine production, protected neuronal architecture, and altered microglia's morphologic and ultrastructural response to HIV-1 Tat exposure in an in vivo murine model of HIV-1 associated neurocognitive disorder. Compound 1 significantly reduces the recruitment of neutrophils into the peritoneum by fMLP in wild-type mice. Compound 1 has demonstrated neuroprotective properties in models of HIV-1 associated neurocognitive disorders (HAND), Alzheimer's disease (AD), Parkinson's disease (PD), multiple sclerosis (MS), perioperative neurocognitive disorders (PND) and delirium superimposed on dementia (DSD), neurotoxic effects of SARS-CoV-2 spike proteins and restoration of the blood-brain barrier (BBB). Compound 1 has demonstrated protection against lipotoxic hepatocyte apoptosis, with anti-inflammatory and anti-fibrotic properties in a murine model of non-alcoholic steatohepatitis (NASH).

Compound 1, however, is insoluble in water and provides only low plasma serum levels of Compound 1 upon administration without excipients such as dimethyl sulfoxide (DMSO) incompatible with human formulations. There is a significant, unmet need for means to administer Compound 1 to treat diseases or disorders, such as diseases or disorders associated with neuroinflammation. The present disclosure fulfills these and other needs, as evident in reference to the following disclosure.

Provided is an acid addition salt of 3-(1H-indol-5-yl)-5-[4-[(4-methyl-1-piperazinyl)methyl]phenyl]-1H-pyrrolo[2,3-b]pyridine selected from a tartrate salt, a phosphate salt, and a fumarate salt. Also provided is a tartrate salt of 3-(1H-indol-5-yl)-5-[4-[(4-methyl-1-piperazinyl)methyl]phenyl]-1H-pyrrolo[2,3-b]pyridine that is substantially crystalline.

Also provided is a pharmaceutical composition comprising an acid addition salt disclosed herein and a pharmaceutically acceptable excipient.

Also provided is a method of treating a disease or disorder, such as a disease or disorder associated with neuroinflammation, comprising administering to a subject in need thereof, a therapeutically effective amount of an acid addition salt disclosed herein, or a pharmaceutical composition of an acid addition salt disclosed herein.

Also provided is a process for preparing an acid addition salt disclosed herein, comprising contacting 3-(1H-indol-5-yl)-5-[4-[(4-methyl-1-piperazinyl)methyl]phenyl]-1H-pyrrolo[2,3-b]pyridine with an acid selected from tartaric acid, fumaric acid, and phosphoric acid in a polar, protic solvent to form an acid addition salt, and isolating the acid addition salt.

As the patent disclosure proceeds, these and other aspects of the invention disclosed herein will be set forth in greater detail.

DRAWINGS

DETAILED DESCRIPTION

Figure 1:
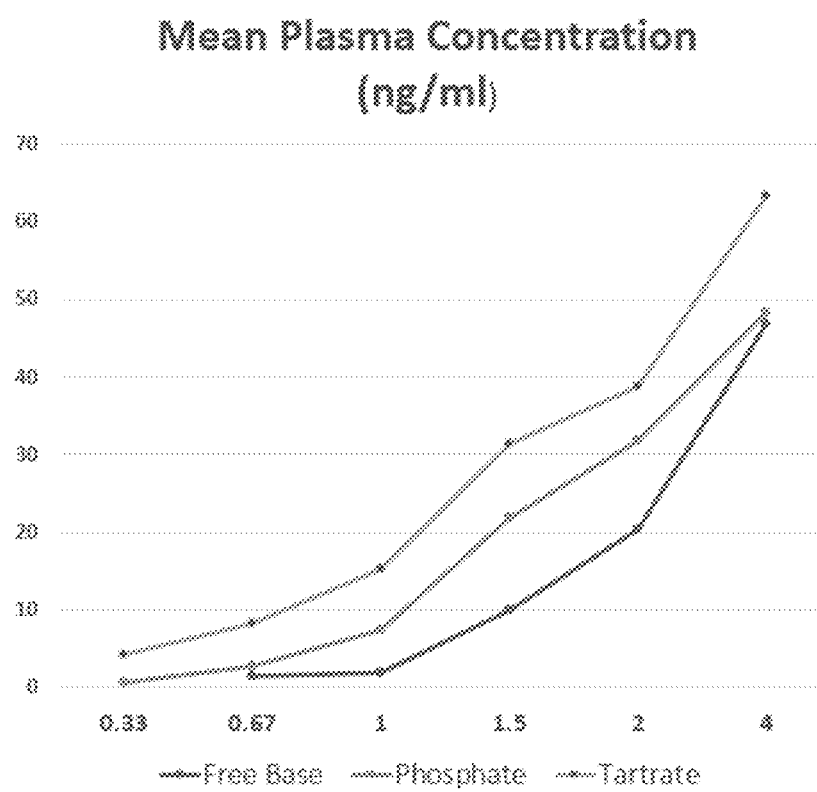
FIG. 1 shows the mean plasma concentrations (ng/mL) over time (hours) in mice for Compound 1 free base, tartrate, and phosphate.

As used in the present specification, the following words and phrases are generally intended to have the meanings as set forth below, except to the extent that the context in which they are used indicates otherwise.

When introducing elements of the present disclosure or in an embodiment, the articles "a," "an," "the," and "said" are intended to mean that there are one or more of the elements. The terms "comprising," "including," and "having" are inclusive and mean that there may be additional elements other than the listed elements.

The term "and/or" when in a list of two or more items means that any of the listed items can be employed by itself or in combination with one or more of the listed items. For example, the expression "A and/or B" means either or both of A and B, i.e., A alone, B alone, or A and B in combination. Likewise, the expression "A, B and/or C" means A alone, B alone, C alone, A and B in combination, A and C in combination, B and C in combination, or A, B, and C in combination.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about" qualifies the numerical values it modifies, denoting such a value as a variable within a margin of error. When no margin of error, such as a standard deviation to a mean value given in a chart or table of data, is recited, the term "about" means that range which would encompass the recited value and the range which would be included by rounding up or down to that figure, considering significant figures.

The term "amorphous" refers to any solid substance which (i) lacks order in three dimensions, or (ii) exhibits order in less than three dimensions, order only over short distances (e.g., less than 10 A), or both. Thus, amorphous substances include partially crystalline materials and crystalline mesophases with, e.g., one- or two-dimensional translational order (liquid crystals), orientational disorder (orientationally disordered crystals), or conformational disorder (conformationally disordered crystals). Amorphous solids may be characterized by known techniques, including X-ray powder diffraction (XRPD) crystallography, solid state nuclear magnet resonance (ssNMR) spectroscopy, differential scanning calorimetry (DSC), or some combination of these techniques. As illustrated, below, amorphous solids give diffuse XRPD patterns, typically comprised of one or two broad peaks (i.e., peaks having base widths of about 5° 2Θ or greater).

The term "polymorph" refers to different crystalline forms of the same compound and includes, but is not limited to, other solid state molecular crystalline forms including hydrates (e.g., bound water present in the crystalline structure) and solvates (e.g., bound solvents other than water) of the same compound.

The term "crystalline" refers to any solid substance exhibiting three-dimensional order, which in contrast to an amorphous solid substance, gives a distinctive XRPD pattern with sharply defined peaks.

The term "substantially crystalline" refers to compounds and/or salts that are at least a particular weight percent crystalline. Particular weight percentages include 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5% and 99.9%. In some embodiments, substantially crystalline refers to a tartrate salt that is at least 70% crystalline. In some embodiments, substantially crystalline refers to a tartrate salt that is at least 80% crystalline. In some embodiments, substantially crystalline refers a tartrate salt that is at least 85% crystalline. In some embodiments, substantially crystalline refers to a tartrate salt that is at least 90% crystalline. In some embodiments, substantially crystalline refers to a tartrate salt that is at least 95% crystalline.

The term "substantially as shown in" when referring, for example, to an XRPD pattern includes a pattern, that may not be necessarily identical to those depicted herein, but that falls within the limits of experimental error or deviations when considered by one of ordinary skill in the art. For example, one skilled in the art will appreciate that the peak positions (2Θ) will show some variability, typically as much as 0.1 to 0.2 degrees, depending on the solvents being used, as well as on the apparatus being used to measure the diffraction. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

Similarly, as used herein, "substantially as shown in" when referring, for example, to solid state NMR spectra and Raman spectra is intended to also encompass the variabilities associated with these analytical techniques, which are known to those of skill in the art. For example, $^{13}C$ chemical shifts measured in solid state NMR will typically have a variability of up to 0.2 ppm for well-defined peaks, and even larger for broad lines, while Raman shifts will typically have a variability of about 2 cm 1 (Raman spectra are typically expressed in ($cm^{-1}$).

The term "solvate" describes a molecular complex comprising the drug substance and a stoichiometric or non-stoichiometric amount of one or more solvent molecules (e.g., ethanol). When the solvent is tightly bound to the drug the resulting complex will have a well-defined stoichiometry that is independent of humidity. When, however, the solvent is weakly bound, as in channel solvates and hygroscopic compounds, the solvent content will be dependent on humidity and drying conditions. In such cases, the complex will often be non-stoichiometric.

The term "hydrate" describes a solvate comprising the drug substance and a stoichiometric or non-stoichiometric amount of water.

The term "channel hydrate" refers to hydrate structures with open structural voids where the water molecules may fully or partly escape through the channels (voids) without significant changes in the crystal structure.

The term "2 theta value" or "2Θ" refers to the peak position in degrees based on the experimental setup of the X-ray diffraction experiment and is a common abscissa unit in diffraction patterns. The experimental setup requires that if a reflection is diffracted when the incoming beam forms an angle theta (Θ) with a certain lattice plane, the reflected beam is recorded at an angle 2 theta (2 Θ). It should be understood that reference herein to specific 2 Θ values for a specific polymorphic form is intended to mean the 2 Θ values (in degrees) as measured using the X-ray diffraction experimental conditions as described herein. For example, as described herein, CuKa (wavelength 1.54056 A) was used as the source of radiation.

The term "disease" as used herein is intended to be generally synonymous, and is used interchangeably with the terms "disorder," "syndrome," and "condition" (as in medical condition), in that all reflect an abnormal condition of the human or animal body or of one of its parts that impairs normal functioning, is typically manifested by distinguishing signs and symptoms and causes the human or animal to have a reduced duration or quality of life.

The term "combination therapy" means administering two or more therapeutic agents to treat a therapeutic condition or disorder described in the present disclosure. Such administration encompasses co-administration of these therapeutic agents in a substantially simultaneous manner, such as in a single capsule having a fixed ratio of therapeutic agents or in multiple, separate capsules for each therapeutic agent. In addition, such administration also encompasses each type of therapeutic agent in a sequential manner. In either case, the treatment regimen will provide beneficial effects of the drug combination in treating the conditions or disorders described herein.

As used herein, "dose" means a quantity of a compound given to the individual for treating or preventing the disease or disorder at one specific time.

As used herein, "in need of treatment" and "in need thereof" when referring to treatment are used interchangeably to mean a judgment made by a caregiver (e.g., physician, nurse, nurse practitioner, etc.) that an individual requires or will benefit from treatment. This judgment is made based on a variety of factors that are in the realm of a caregiver's expertise, but that includes the knowledge that the individual is ill, or will become ill, as the result of a disease, condition, or disorder that is treatable by the salts described herein. Accordingly, the salts described herein can be used in a protective or preventive manner; or the salts described herein can be used to alleviate, inhibit or ameliorate the disease, condition, or disorder.

"Patient" is generally synonymous with "subject" and includes all mammals, including humans. Examples of patients include humans, livestock such as cows, goats, sheep, pigs, and rabbits, and companion animals such as dogs, cats, rabbits, and horses. In certain embodiments, the patient is a human.

As used herein, the term "prevent," "preventing," or "prevention," such as prevention of a particular disorder or the occurrence or onset of one or more symptoms associated with the particular disorder and does not necessarily mean the complete prevention of the disorder. For example, the term "prevent," "preventing," and "prevention" means the administration of therapy on a prophylactic or preventative basis to an individual who may ultimately manifest at least one symptom of a disease or condition but who has not yet done so. Such individuals can be identified based on risk factors known to correlate with the subsequent occurrence of the disease. Alternatively, prevention therapy can be administered without prior identification of a risk factor as a prophylactic measure. Delaying the onset of at least one symptom can also be considered prevention or prophylaxis.

As used herein, the "therapeutically effective amount" of a therapeutic agent, composition, or combination is an amount that is nontoxic and effective for producing some desired therapeutic effect upon administration to a subject or patient (e.g., a human subject or patient). The precise therapeutically effective amount for a subject may depend upon, e.g., the subject's size and health, the nature and extent of the condition, the therapeutics or combination of therapeutics selected for administration, and other variables known to those of skill in the art. The effective amount for a given situation is determined by routine experimentation and is within the clinician's judgment. In some embodiments, the therapeutically effective amount is the standard dose.

As used herein, the term "treat," "treating," or "treatment" means the administration of therapy to an individual who already manifests at least one symptom of a disease or condition or who has previously manifested at least one symptom of a disease or condition. For example, "treating" can include alleviating, abating, or ameliorating a disease or condition symptoms, preventing additional symptoms, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. For example, the term "treating" in reference to a disorder means reducing the severity of one or more symptoms associated with that particular disorder. Therefore, treating a disorder does not necessarily mean a reduction in the severity of all symptoms associated with a disorder and does not necessarily mean a complete reduction in the severity of one or more symptoms associated with a disorder.

When an integer is used in a method disclosed herein, the term "about" can be inserted before the integer.

Throughout this specification, unless the context requires otherwise, the word "comprise," or variations such as "comprises" or "comprising" will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps, or group of compositions of matter shall be taken to encompass one and a plurality (i.e., one or more) of those steps, compositions of matter, groups of steps, or groups of compositions of matter.

Each embodiment described herein is to be applied mutatis mutandis to each and every other embodiment unless specifically stated otherwise.

Those skilled in the art will appreciate that the invention(s) described herein is susceptible to variations and modifications other than those specifically described. It is to be understood that the invention(s) includes all such variations and modifications. The invention(s) also includes all the steps, features, compositions, and compounds referred to or indicated in this specification, individually or collectively, and any and all combinations or any two or more of said steps or features unless specifically stated otherwise.

The present invention(s) is not to be limited in scope by the specific embodiments described herein, which are intended for exemplification only. Functionally equivalent products, compositions, and methods are clearly within the scope of the invention(s), as described herein.

It is appreciated that certain features of the invention(s), which are, for clarity, described in the context of separate embodiments, can also be provided in combination in a single embodiment. Conversely, various features of the invention(s), which are, for brevity, described in the context of a single embodiment, can also be provided separately or in any suitable sub-combination.

Acid Addition Salts

Provided is an acid addition salt of 3-(1H-indol-5-yl)-5-[4-[(4-methyl-1-piperazinyl)methyl]phenyl]-1H-pyrrolo[2,3-b]pyridine selected from a tartrate salt, a phosphate salt, and a fumarate salt.

In certain embodiments, the acid addition is a tartrate salt. In certain embodiments, the tartrate salt is a (D)-(−)tartrate salt. In certain embodiments, the tartrate salt is a (L)-(+) tartrate salt. In certain embodiments the tartrate salt is a mixture of a (L)-(+) tartrate salt and a (D)-(−)-tartrate salt.

In certain embodiments, the acid addition salt is a phosphate salt.

In certain embodiments, the acid addition salt is a fumarate salt.

Also provided is a tartrate salt of 3-(1H-indol-5-yl)-5-[4-[(4-methyl-1-piperazinyl)methyl]phenyl]-1H-pyrrolo[2,3-b]pyridine that is substantially crystalline.

In certain embodiments, the tartrate salt is substantially Form 1.

In certain embodiments, the tartrate salt is a mixture of an (L)-(+) tartrate salt and a (D)-(−)-tartrate salt.

In certain embodiments, the tartrate salt has a molar ratio of tartaric acid to Compound 1 of about 1:1.

In certain embodiments, the tartrate salt is characterized by an x-ray powder diffraction (XRPD) pattern comprising peaks, in units 2-theta, at 16.1±0.2, 17.6±0.2, 21.3±0.2, and 22.8±0.2.

In certain embodiments, the tartrate salt is characterized by an XRPD pattern comprising three or more peaks, in units of 2-theta, selected from 4.7±0.2, 6.8±0.2, 8.5±0.2, 9.5±0.2, 11.3±0.2, 13.1±0.2, 18.9±0.2, 26.6±0.2, 28.3±0.2, 31.6±0.2, 35.2±0.2, 40.9±0.2, 45.0±0.2, and 48.8±0.2.

Figure 2:
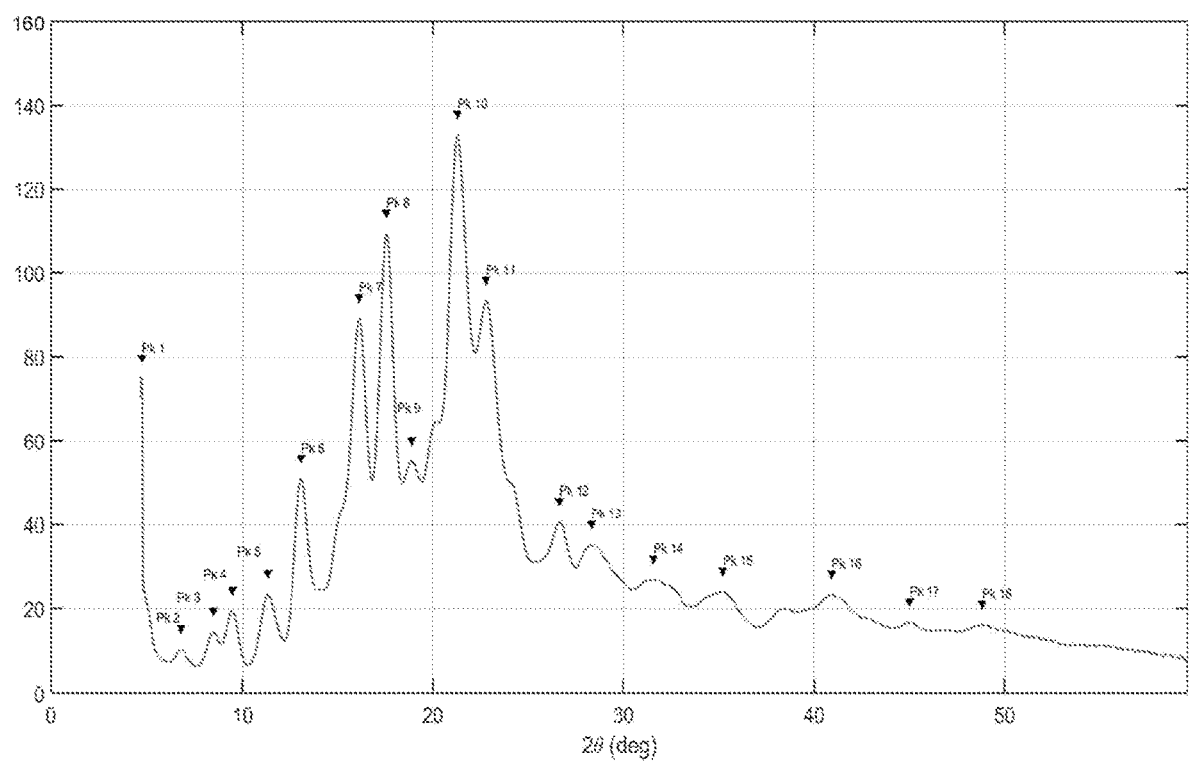
FIG. 2 shows an x-ray diffractogram obtained from XRPD analysis for the tartrate salt of Compound 1.

In certain embodiments, the tartrate salt is characterized by an XRPD pattern as substantially shown in FIG. 2.

Also provided is a process for preparing an acid addition salt of claim 1, comprising: contacting 3-(1H-indol-5-yl)-5-[4-[(4-methyl-1-piperazinyl)methyl]phenyl]-1H-pyrrolo[2,3-b]pyridine with an acid selected from tartaric acid, fumaric acid, and phosphoric acid in a polar, protic solvent to form an acid addition salt, and isolating the acid addition salt.

In certain embodiments, the 3-(1H-indol-5-yl)-5-[4-[(4-methyl-1-piperazinyl)methyl]phenyl]-1H-pyrrolo[2,3-b]pyridine and acid are mixed in a ratio between 1:2 and 2:1 then dissolved in the polar, protic solvent. In certain embodiments, the ratio is 1:1.

Suitable polar, protic solvents include, but are not limited to, water, methanol, ethanol, and acetic acid. In certain embodiments, the polar, protic solvent is methanol. In certain embodiments, the polar, protic solvent is ethanol.

In certain embodiments, the polar, protic solvent is heated. In certain embodiments, the methanol is heated.

In certain embodiments, the isolating step comprises adding ether until the solution of the contacting step is cloudy.

In certain embodiments, the isolating step comprises allowing the solution of the contacting step to remain until a solid precipitates. In certain embodiments, the solid is filtered and washed with ether. In certain embodiments, the isolated addition salt is dissolved in hot ethanol, cooled, and precipitated as a powder.

Pharmaceutical Composition

While the disclosed salts may be administered as raw chemicals, presenting them as a pharmaceutical formulation is also possible. Accordingly, also provided is a pharmaceutical composition comprising an acid addition salt described herein and a pharmaceutically acceptable excipient.

In certain embodiments, unit dosage formulations contain an effective dose, or an appropriate fraction thereof, of the therapeutic agent.

The salts described herein may be administered orally or via injection at a dose of 300 µg/kg to 25 mg/kg per day (free base equivalent). The dose range for adult humans is generally from 0.02 g/day to 2 g/day (free base equivalent).

Proper formulation depends upon the route of administration chosen. Any well-known technique, carrier, or excipient may be suitable and understood in the art. The pharmaceutical compositions disclosed herein may be manufactured in any manner known in the art, e.g., conventional mixing, dissolving, granulating, dragee-making, levigating, emulsifying, encapsulating, entrapping, entrapping, or compressing processes.

The salts described herein can be administered in various modes. The most suitable route may depend upon, for example, the condition and disorder of the recipient. The formulations may conveniently be presented in unit dosage form and may be prepared by any of the methods well known in the art of pharmacy. In certain embodiments, the salts disclosed herein are administered orally.

Pharmaceutical preparations that can be used orally include tablets, push-fit capsules made of gelatin ("gelcaps"), and soft, sealed capsules made of gelatin and a plasticizer, such as glycerol or sorbitol ("softgels").

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active, or dispersing agents. Molded tablets may be made by molding a mixture of the powdered compound moistened with an inert liquid diluent in a suitable machine. The tablets may optionally be coated or scored and formulated to provide a slow or controlled release of the active ingredient therein.

The push-fit capsules can contain the active ingredients in admixture with filler such as lactose, binders such as starches, and/or lubricants such as talc or magnesium stearate and, optionally, stabilizers.

In soft capsules, the active compounds may be dissolved or suspended in suitable liquids, such as fatty oils, liquid paraffin, or liquid polyethylene glycols. In addition, stabilizers may be added.

In certain embodiments, the salts disclosed herein are orally administered in a suspension. When present, the suspension comprises undissolved particles of a salt disclosed herein, mixed with a liquid vehicle, such as water. In certain embodiments, the suspension comprises Compound 1 tartrate dose equimolarly compared to the free base of Compound 1. In certain embodiments, the suspension comprises Compound 1 phosphate dose equimolarly compared to the free base of Compound 1. In certain embodiments, the suspension may further comprise a complexing agent to stabilize the suspension during storage.

The precise amount administered to a patient will be the responsibility of the attendant physician. The specific dose level for any patient will depend upon a variety of factors, including the activity of the specific salt employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the salts described herein in combination with another therapeutic agent. The multiple therapeutic agents (at least one of which is a salt disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given in multiple doses. If not simultaneous, the timing between the multiple doses may be any duration of time ranging from a few min to four weeks.

Methods of Treatment

Also provided are methods of treating a disease or disorder, comprising administering to a subject in need thereof, a therapeutically effective amount of an acid addition salt disclosed herein, or the pharmaceutical composition of an acid addition salt disclosed herein.

In certain embodiments, the disease or disorder is a disease or disorder associated with neuroinflammation.

In certain embodiments, the disease or disorder associated with neuroinflammation is a neurodegenerative disorder. In certain embodiments, the neurodegenerative disorder is chosen from Alzheimer's dementia, HIV-1 associated dementia, spongiform encephalopathy, Creutzfeldt-Jakob disease, stroke, trauma, multiple sclerosis, Parkinson's disease, tauopathies including progressive supranuclear palsy and frontotemporal dementia, HIV infection of the central nervous system, HIV associated neurocognitive disorder (HAND), hereditary hemorrhage with amyloidosis-Dutch type, cerebral amyloid angiopathy, and Down's syndrome.

The methods of treating may also reduce or alleviate a symptom of a neurodegenerative disorder. These symptoms include, but are not limited to, memory loss, forgetfulness, apathy, anxiety, agitation, a loss of inhibition, poor cognitive abilities, deficits in cortical sensory modalities, difficulty reading and writing, and mood changes. Other symptoms of neurodegenerative disorders affect how the body functions, including, but not limited to, partial or complete paralysis, muscle weakness, partial or complete loss of sensation, seizures, unexplained pain, and decreased alertness.

In certain embodiments, the disease or disorder is drug-induced peripheral neuropathy, and diabetic neuropathy, and HIV-associated neuropathy, ototoxicity and hearing loss, acute insults to the inner ear, including acoustic trauma, blast noise (for example, as experienced by military personnel), exposure to ototoxic chemotherapeutic agents for cancer therapy (such as cisplatin) and treatment with aminoglycoside antibiotics.

In certain embodiments, the disease or disorder is a psychological disorder including depression or major depressive disorder (MDD), bipolar disorder, and post-traumatic stress disorder.

In certain embodiments, the disease or disorder is chosen from metabolic diseases such as type 1 and type 2 diabetes mellitus, hyperglycemia, diabetic complications (such as retinopathy, nephropathy, neuropathy, ulcers, micro- and macroangiopathies, gout and diabetic foot disease), insulin resistance, metabolic syndrome (Syndrome X), hyperinsulinemia, hypertension, hyperuricemia, obesity, edema, dyslipidemia, hepatic steatosis, non-alcoholic steatohepatitis (NASH), chronic heart failure, atherosclerosis, peripheral inflammation and hepatitis, including viral hepatitis, and metabolic associated fatty liver disease (MAFLD).

In certain embodiments, the disease or disorder is a proliferative disorder, such as liver cancer, pancreatic ductal adenocarcinoma, glioblastoma, or metastatic breast cancer.

In certain embodiments, the disease or disorder is an inflammatory disease such as bacterial sepsis, otitis media, endotoxemia, mucosal hyperplasia, inflammatory bowel disease, Crohn's disease, irritable bowel syndrome, and ulcerative colitis; and respiratory diseases and conditions such as asthma, chronic obstructive pulmonary disease (COPD), and acute inhalation-induced lung injury.

In certain embodiments, the disease or disorder is an autoimmune disease such as multiple sclerosis, rheumatoid arthritis, lupus and Crohn's disease.

In certain embodiments, the disease or disorder is an ischemic injury, including traumatic brain injury such as stroke, subarachnoid hemorrhage, cerebral ischemia/reperfusion, myocardial infarction, and ischemic heart disease.

In certain embodiments, the disease or disorder is pain including inflammatory pain, neuropathic pain, back pain including discogenic pain, the pain of arthritis and autoimmune disorders such as rheumatoid arthritis, and cancer pain including pain due to bone metastasis.

In certain embodiments, the method is for the treating and/or preventing of a cytokine storm, delirium or delirium superimposed on dementia in a patient infected by SARS-CoV-2, a patient having COVID-19, or a patient having MAFLD associated with end organ damage.

EXAMPLES

Example 1—Salt Screen and Preparation

Compound 1 has limited solubility in typical aqueous and organic carriers. To improve solubility, attempts to prepare acid addition salts from suitably acidic carboxylic acids (e.g., fumaric acid, maleic acid, citric acid, tartaric acid), standard mineral acids (e.g., hydrobromic acid, sulfuric acid, phosphoric acid), and sulfonic acids (e.g., toluenesulfonic acid, methanesulfonic acid, ethanesulfonic acid, benzenesulfonic acid), were conducted.

Dual solvent systems were used, comprising methanol and ether, by dissolving the salt in a small volume of methanol and then adjusting the solubility by adding ether to the point of slight cloudiness. These samples then remained in the reaction vessel as needed to precipitate. For several salts, ethanol and 95% ethanol were also explored, but the salts were generally insoluble in these latter solvents, even when well-diluted.

Phosphoric Acid

A methanol solution containing one molar equivalent of 48% aqueous phosphoric acid was added to a methanol solution of Compound 1 to obtain a homogeneous solution. The solvent was removed under reduced pressure and pumped dry to remove trace water from the aqueous phosphoric acid. The residue was dissolved in a small volume of methanol (with heating, then cooling to room temperature), and ether was added. The solid precipitate formed almost immediately. The solubility of this white powder salt was low in methanol; lower than the other acid salts disclosed herein.

With heating, it dissolved but precipitated upon cooling a concentrated solution. The white power was collected, washed with ether, and dried. $C_{27}H_{30}N_5O_4P$. MW=520 g/mol. Calculated for the mono salt: C, 62.42; H, 5.82; N, 13.48; O, 12.32; P, 5.96. Found: C, 61.95; H, 5.99; N, 13.22.

Fumaric Acid

Compound 1 and fumaric acid were mixed in a 1:1 molar ratio and heated in a small volume of methanol to dissolve. The mixture was cooled, and ether was added until cloudy. The solution was allowed to stand, affording a white powder, which was filtered, and washed with ether. The solids could also be dissolved in hot ethanol with subsequent cooling to precipitate the white powder. $C_{31}H_{33}N_5O_6^-$. MW=572 g/mol. Calculated for the mono salt: C, 65.14; H, 5.82; N, 12.25; O, 16.79. Found C, 65.89, H 6.13, N 13.05.

Tartaric Acid

Compound 1 and tartaric acid were mixed in a 1:1 molar ratio and heated in a small volume of methanol to dissolve. After cooling, ether was added to the point of cloudiness. A solid precipitated upon standing. The precipitate was filtered and washed with ether. This filtered powder was not very soluble in methanol but would dissolve to some extent with heating. The resulting crystalline material was analyzed using XRPD to provide the spectrum shown in FIG. 2.

The tartrate salt exhibited an unusual behavior with water. As increasing volumes of water were added to the dry powder and heated, the sample went from being a slurry to a homogeneous gel to a free-flowing solution. Upon cooling and examination during this process, the material progressed from being a slurry, to a clear viscous gel; after adding additional water the gel dissolved with continued heating to obtain a free-flowing solution. When the sample was cooled, the solution remained homogeneous. When the gel was inverted, it would flow after a minute. The gel-like solution could also be transferred using a pipette. Standing for a couple of days did not change the sample's appearance or behavior. The gel-like appearance could be diluted by water to obtain a free-flowing homogeneous solution, or the gel form could be heated to obtain a typical solution (but again formed the gel upon cooling). Optically pure D- and L-tartaric acid was used. Calculated for the mono salt: C, 67.47; H, 6.19; N, 12.29. Found: C, 65.89; H, 6.13; N, 13.05.

Maleic Acid

The same procedure was used for maleic acid as on its isomer, fumaric acid. The solution precipitated after storing overnight in the refrigerator, but the precipitate was somewhat viscid and did not filter well.

Citric Acid

Compound 1 and citric acid were mixed in a 1:1 molar ratio and subjected to the methanol/ether treatment. A viscid material was obtained with no solid precipitate.

Sulfuric Acid

When methanol solution containing one equivalent of sulfuric acid was added to a methanol solution of Compound 1, a taffy-like glue immediately precipitated, even when repeated under much more dilute conditions. Attempts to dissolve this material were unsuccessful, even with significant dilution with methanol or heating.

Hydrobromic Acid

One molar equivalent of hydrobromic acid (using a solution of 33% hydrogen bromide in acetic acid) was added to a methanol solution of Compound 1. The homogeneous solution was repeatedly dried under reduced pressure, placed under sustained vacuum, and redissolved in methanol to remove remnants of the acetic acid. The residue was then dissolved in methanol. Ether was added until initial cloudiness and then allowed to stand. Viscid solids were obtained. When repeated, the solution was diluted. Ethanol and 95% ethanol were also tried. The viscid solids were not very soluble in methanol.

Organic Sulfonic Acids (TolSO$_3$H, PhSO$_3$H, MeSO$_3$H, EtSO$_3$H)

Compound 1 and an organic sulfonic acid were mixed after weighting out in a 1:1 molar ratio. Each showed good solubility in methanol. Still, in every case, adding ether to the initial point of cloudiness resulted in the salt precipitating in a thin film of viscous liquid on the vial wall and bottom. Cold storage, scratching, and increasing the dilution were unsuccessful at preparing the acid addition salt. The thin-film viscous liquid refused to solidify or crystallize.

Solubility

Water was mixed with the salt and heated with repeated vortexing and sonication, ensuring that salt solids remained present to ensure saturation. Samples were allowed to stand for 1 hr and then filtered through a syringe filter. An aliquot was removed via pipette and diluted 4× using methanol to prevent subsequent precipitation. The solutions remained homogeneous. Using an Agilent HPLC-MS, each was injected using an autosampler that has been previously validated to give repeatable injection volumes, as determined by comparing "total area" integration at two UV wavelengths.

The free base solid floated on the water when mixing excess freebase with water without heating. In contrast, the three acid addition salts sank to the bottom, easily distinguishing them from the free base powder.

The free base was not very soluble in methanol, ethanol, or 95% ethanol at room temperature but did dissolve upon heating or substantial dilution. Salts prepared from fumaric acid, tartaric acid, and phosphoric acid resulted in powder solids that dissolved in methanol, ethanol, or 95% ethanol. The phosphate was the least soluble in methanol of the three salts tested. The fumarate and tartrate dissolved readily in hot methanol.

Summary

Pharmaceutically acceptable salts were prepared using tartaric acid, fumaric acid, and phosphoric acid. The tartrate was the fastest to kinetically dissolve. When heated with a small volume of water, the tartrate afforded a homogeneous gelatin-like material that became a free-flowing solution after adding more water.

The melting points and relative water solubility of the acid addition salts are shown below.

TABLE 1

Physical properties of addition salts

| Compound | Melting point | Relative water solubility |
| --- | --- | --- |
| Free base | 223-226° C. | 1.0 |
| Fumarate | 244° C.* | 0.59 |
| Phosphate | 244° C.* | 0.31 |
| Tartrate | 230° C. | 1.12 |

*broad melting range; appeared to decompose

Example 2—X-Ray Powder Diffraction (XRPD)

A sample of the tartrate salt as prepared above was packed into a borosilicate capillary tube (1.0 mm OD, 0.01 mm wall thickness), which was then flame sealed. A second empty capillary tube was prepared in the same way to collect a background. X-ray data were collected at room temperature (292.3 K) on a Rigaku XtaLAB Synergy-S diffraction system equipped with a HyPix-6000HE HPC detector and controlled by CrysalisPro, v42.59a. CuKα radiation (λ=1.54184 Å; slit fully open, 9.0 mR) was generated by a PhotonJet-S microfocus source operated at 50 kV, 1 mA.

At a sample-to-detector distance of 34 mm, φ was rotated through 720 degrees in 300 s (2.4 degrees/s) with ω=−52.16, θ=0.00 and κ=134.00 degrees.

The background image was then subtracted from the sample image to yield the data described herein.

Example 3—Testing in Mice

We measured the pharmacokinetic behaviors of the salts in vivo when dosed under conditions that would mimic administration of Compound 1 as a typical solid tablet or pill. Aqueous suspensions of the free base, the phosphate, and the tartrate were equimolarly dosed in mice at a mass ratio of 1.00, 1.36, and 1.23 to account for the contribution of the acid component to the formula weight. The free base and its phosphate and tartrate salts were dosed at equivalent levels of active drugs. Still, due to the added formula weight contribution of the phosphoric acid and tartaric acid, these two salt forms were dosed at slightly higher gross weight levels so that the dose contained the same 10 mg/kg of the free base drug.

Blood was sampled with microbleeds frequently to produce the pharmacokinetics curves (AUCs). Both salts gave better exposure, as shown by a larger AUC, shorter $T_{max}$, and larger $C_{max}$.

The dosing suspension was analyzed before administration to the animals to ensure that the actual concentration was known. The AUC values were directly comparable since the three samples were dosed at the same drug level as the free base. The $AUC_{last}$ represents the AUC (area under the curve) or total amount of drug in circulating plasma over the time-course of the 6-hour study and is the parameter associated with calculating oral bioavailability of a dosed drug.

The mean plasma levels during the first four hours are depicted in Table 3 and the figure. As can be seen by the $C_{max}$, the better solubility and faster dissolution rate of the phosphate and tartrate salts compared to the free base results in more rapid and complete absorption during the first four hours after dosing (Table 2). Examining the $T_{max}$ shows that the tartrate salt was the most rapidly absorbed, followed by the phosphate and the free base. The $T_{max}$ values for the free base and phosphate showed that they took longer to attain peak concentration in plasma than the tartrate. The $T_{max}$ for the tartrate salt was attained the most rapidly. This also suggested faster dissolution for the tartrate salt over the phosphate salt or the free base although the phosphate was still superior to the free base in key pharmacokinetic measures

TABLE 2

Plasma concentrations of Compound 1 after dosing.

| | Free base | Phosphate | Tartrate |
|---|---|---|---|
| $C_{max}$ (ng/ml) | 56.3 | 78 | 66.9 |
| $AUC_{last}$ (hr * ng/ml) | 181 | 230 | 259 |
| $T_{max}$ (hrs) | 6.00 | 6.00 | 4.67 |
| Mean ng/ml at 0.33 hr | LLQ | 0.679 | 4.24 |
| Mean ng/ml at 0.67 hr | 1.46 | 2.71 | 8.2 |
| Mean ng/ml at 1.0 hr | 1.91 | 7.32 | 15.2 |
| Mean ng/ml at 1.5 hr | 10.0 | 21.9 | 31.4 |
| Mean ng/ml at 2.0 hr | 20.4 | 31.7 | 38.8 |
| Mean ng/ml at 4.0 hr | 46.9 | 48.3 | 63.4 |

"LLQ" refers to lower limit of quantification

When one compares standard deviations for similar ng/ml plasma concentrations, the free base is more variable than the phosphate but not the tartrate.

TABLE 3

Variability of Compound 1 concentration in plasma after dosing.

| | Free base | | Phosphate | | Tartrate | |
|---|---|---|---|---|---|---|
| | Mean ng/ml | SD | Mean ng/ml | SD | Mean ng/ml | SD |
| Mean ng/ml at 0.33 hr | LLQ | NK | 0.679 | 0.11 | 4.24 | 4.83 |
| Mean ng/ml at 0.67 hr | 1.46 | 0.88 | 2.71 | 0.67 | 8.2 | 4.6 |
| Mean ng/ml at 1.0 hr | 1.91 | 0.98 | 7.32 | 1.12 | 15.2 | 8.6 |
| Mean ng/ml at 1.5 hr | 10.0 | 4.9 | 21.9 | 2.9 | 31.4 | 14.7 |
| Mean ng/ml at 2.0 hr | 20.4 | 13.6 | 31.7 | 3.5 | 38.8 | 15.0 |
| Mean ng/ml at 4.0 hr | 46.9 | 15.9 | 48.3 | 9.4 | 63.4 | 15.3 |

"LLQ" refers to lower limit of quantification; "NK" refers to not know.

All references, patents, or applications, U.S. or foreign, cited in the application are hereby incorporated by reference as if written herein in their entireties. Where any inconsistencies arise, the material disclosed herein controls.

From the foregoing description, one skilled in the art can easily ascertain the essential characteristics of this invention. Then, without departing from the spirit and scope thereof, one can make various changes and modifications of the invention to adapt it to various usages and conditions.

What is claimed is:

1. A method of treating a disease or disorder associated with neuroinflammation, comprising administering to a subject in need thereof, a therapeutically effective amount of a tartrate salt of 3-(1H-indol-5-yl)-5-[4-[(4-methyl-1-piperazinyl)methyl]phenyl]-1H-pyrrolo[2,3-b]pyridine
    wherein said disease or disorder is chosen from Alzheimer's dementia, perioperative neurocognitive disorders (PND) and delirium superimposed on dementia (DSD), HIV-1 associated dementia, spongiform encephalopathy, Creutzfeldt-Jakob disease, stroke, trauma, multiple sclerosis, Parkinson's disease, tauopathies including progressive supranuclear palsy and frontotemporal dementia, HIV infection of the central nervous system, hereditary hemorrhage with amyloidosis-Dutch type, cerebral amyloid angiopathy, and Down's syndrome: and
    wherein said tartrate salt of 3-(1H-indol-5-yl)-5-[4-[(4-methyl-1-piperazinyl)methyl]phenyl]-1H-pyrrolo[2,3-b]pyridine is characterized by an XRPD pattern comprising three or more peaks, in units of 2-theta, selected from 4.7±0.2, 6.8±0.2, 8.5±0.2, 9.5±0.2, 11.3±0.2, 13.1±0.2, 18.9±0.2, 26.6±0.2, 28.3±0.2, 31.6±0.2, 35.2±0.2, 40.9±0.2, 45.0±0.2, and 48.8±0.2.

2. The method of claim 1, wherein the tartrate salt is substantially Form 1.

3. The method of claim 1, wherein the tartrate salt is a mixture of an (L)-(+) tartrate salt and a (D)-(−)-tartrate salt.

4. The method of claim 1, having a molar ratio of tartaric acid to 3-(1H-indol-5-yl)-5-[4-[(4-methyl-1-piperazinyl)methyl]phenyl]-1H-pyrrolo[2,3-b]pyridine of about 1:1.

5. The method of claim 1, characterized by an x-ray powder diffraction (XRPD) pattern comprising peaks, in units 2-theta, at 16.1±0.2, 17.6±0.2, 21.3±0.2, and 22.8±0.2.

6. The method of claim 1, characterized by an XRPD pattern as substantially shown in FIG. 2.

* * * * *